US009830501B2

(12) United States Patent
Backman et al.

(10) Patent No.: US 9,830,501 B2
(45) Date of Patent: Nov. 28, 2017

(54) HIGH THROUGHPUT PARTIAL WAVE SPECTROSCOPIC MICROSCOPY AND ASSOCIATED SYSTEMS AND METHODS

(71) Applicant: NORTHWESTERN UNIVERSITY, Evanston, IL (US)

(72) Inventors: Vadim Backman, Chicago, IL (US); Hariharan Subramanian, Chicago, IL (US); John E. Chandler, Evanston, IL (US); Craig White, Royal Oak, MI (US); Jeremy D. Rogers, Madison, WI (US); Lusik Cherkezyan, Evanston, IL (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 380 days.

(21) Appl. No.: 14/339,239

(22) Filed: Jul. 23, 2014

(65) Prior Publication Data
US 2015/0029326 A1    Jan. 29, 2015

Related U.S. Application Data

(60) Provisional application No. 61/857,427, filed on Jul. 23, 2013.

(51) Int. Cl.
*G06K 9/00* (2006.01)
*G02B 21/36* (2006.01)
(Continued)

(52) U.S. Cl.
CPC ........ *G06K 9/00127* (2013.01); *G01J 3/1256* (2013.01); *G01J 3/2823* (2013.01);
(Continued)

(58) Field of Classification Search
CPC .......... G01J 3/1256; G01J 3/2823; G01J 3/44; G01N 2021/4709; G01N 21/47;
(Continued)

(56) References Cited

U.S. PATENT DOCUMENTS 5,827,629 A * 10/1998 Miyatake .................. G03F 9/70
250/559.3
7,336,352 B2 * 2/2008 Tanaka .................. G03F 9/7003
356/306

(Continued)

FOREIGN PATENT DOCUMENTS

WO    WO/01/75502    10/2011

OTHER PUBLICATIONS

Bernstein et al., "Field defects in progression to gastrointestinal tract cancers," Cancer Lett, 260(1-2): 1-10, 2008.
(Continued)

*Primary Examiner* — Anner Holder
(74) *Attorney, Agent, or Firm* — Perkins Coie LLP

(57) ABSTRACT

The present technology provides methods, systems, and apparatuses to achieve high throughput and high speed acquisition of partial wave spectroscopic (PWS) microscopic images. In particular, provided herein are high-throughput, automated partial wave spectroscopy (HT/A-PWS) instruments and systems capable of rapid acquisition of PWS Microscopic images and clinical, diagnostic, and research applications thereof.

26 Claims, 7 Drawing Sheets

(51) Int. Cl.
| | |
|---|---|
| H04N 5/235 | (2006.01) |
| H04N 5/232 | (2006.01) |
| G01J 3/44 | (2006.01) |
| G01J 3/12 | (2006.01) |
| G01J 3/28 | (2006.01) |
| G02B 21/06 | (2006.01) |
| G02B 21/16 | (2006.01) |
| G01N 21/47 | (2006.01) |

(52) U.S. Cl.
CPC .............. *G01J 3/44* (2013.01); *G01N 21/47* (2013.01); *G02B 21/06* (2013.01); *G02B 21/16* (2013.01); *G02B 21/365* (2013.01); *H04N 5/2354* (2013.01); *H04N 5/23212* (2013.01); *G01N 2021/4709* (2013.01)

(58) Field of Classification Search
CPC ...... G02B 21/06; G02B 21/16; G02B 21/365; G06K 9/00127; H04N 5/23212; H04N 5/2354
USPC .......................................................... 348/80
See application file for complete search history.

(56) References Cited

U.S. PATENT DOCUMENTS

| | | | |
|---|---|---|---|
| 7,652,772 | B2 | 1/2010 | Backman et al. |
| 7,667,832 | B2 | 2/2010 | Backman et al. |
| 7,800,746 | B2 | 9/2010 | Backman et al. |
| 8,131,348 | B2 | 3/2012 | Backman et al. |
| 8,735,075 | B2 | 5/2014 | Backman et al. |
| 9,090,933 | B2 | 7/2015 | Backman et al. |
| 2006/0155178 | A1 | 7/2006 | Backman et al. |
| 2008/0180664 | A1 | 7/2008 | Backman et al. |
| 2008/0278713 | A1 | 11/2008 | Backman et al. |
| 2012/0214880 | A1 | 8/2012 | Backman et al. |
| 2015/0029236 | A1 | 1/2015 | De Greef |
| 2015/0185151 | A1* | 7/2015 | Utzinger ............ A61B 1/00009 356/51 |

OTHER PUBLICATIONS

Dakubo et al., "Clinical implications and utility of field cancerization," Cancer Cell International, 7(2): 2007.

Roy et al., "Partial Wave Spectroscopy Microscopy (PWS) Analysis of Fecal Colonocytes for Field Carcinogenesis Detection: A Novel Modality for Colorectal Cancer (CRC) Screening," Gastroenterology 138(5):S194 (May 2010).

Roy et al., "Detection of the colorectal cancer (CRC) field effect through partial wave spectroscopic microscopy (PWS)," Gastroenterology, vol. 132, No. 4, Suppl. 2 (Apr. 2007).

Subramanian et al., "Nanoscale cellular changes in field carcinogenesis detected by partial wave spectroscopy," Cancer Res, 69(13): 5357-5363, 2009.

Subramanian et al., "Optical methodology for detecting histologically unapparent nanoscale consequences of genetic alterations in biological cells," Proc Nail Acad Sci USA, 105(51): 20118-20123,2008.

Subramanian et al., "Partial-wave microscopic spectroscopy detects subwavelength refractive index fluctuations: an application to cancer diagnosis," Optics Letters, 34(4): 518-520, 2009.

* cited by examiner

HIGH THROUGHPUT PARTIAL WAVE SPECTROSCOPIC MICROSCOPY AND ASSOCIATED SYSTEMS AND METHODS

RELATED APPLICATIONS INCORPORATED BY REFERENCE

The present application claims priority to U.S. Provisional Patent Application No. 61/857,427, filed Jul. 23, 2013, entitled "HIGH THROUGHPUT PARTIAL WAVE SPECTROSCOPIC MICROSCOPY," which is incorporated herein in its entirety by reference.

STATEMENT REGARDING FEDERAL FUNDING

This invention was made with government support under Grant Nos. R01 CA165309, RO1-CA155284, and 1R44CA168185 awarded by the National Institutes of Health, and Grant No. IIP-1214989 awarded by the National Science Foundation. The government has certain rights in the invention.

TECHNICAL FIELD

The present technology provides methods, systems, and apparatuses to achieve high throughput and high speed acquisition of partial wave spectroscopic (PWS) microscopic images. In particular, provided herein are high-throughput, automated partial wave spectroscopy (HT/A-PWS) instruments and systems capable of rapid acquisition of PWS Microscopic images, and clinical, diagnostic, and research applications thereof.

BACKGROUND

In Partial Wave Spectroscopy (PWS), a focused wave of broadband, low-spatially-coherent light illuminates a sample, and an image formed by back-scattered photons is acquired in the far field. A spectrum of the back-scattered light intensity is recorded for each pixel of the image. PWS combines certain aspects of microscopy and the spectroscopy of light elastically scattered by cells. However, unlike conventional microscopy, in which an image is formed by integrating the reflected or transmitted intensity over a broad spectrum, PWS measures spectral fluctuations in the back-scattering spectra. Unlike elastic scattering spectroscopy, where a signal is formed by the far-field interference of all waves propagating within a scattering particle, the spectrum analyzed in PWS is formed by a subset of these waves (a.k.a., "partial waves").

When applied to a sample comprising cells, PWS virtually divides a cell into a collection of parallel channels each with a diffraction-limited transverse size, detects back-scattered waves propagating along 1D trajectories within these channels, and quantifies the statistical properties of the nanoarchitecture of a cell by the analysis of the fluctuating part of the (normalized) reflected intensity $R(\lambda, x, y)$, where $\lambda$ is the wavelength of light, and x and y are the spatial coordinates of a particular channel. By allowing analysis of the nanoarchitecture of cells in a sample, PWS is capable of detecting nanoarchitectural alterations in cells that are otherwise histologically indistinguishable.

First generation PWS instruments perform a single measurement in 3-4 minutes per cell. When combined with time for position selection and focusing, a sample of at least 30 cells, a number commonly required for diagnosis, requires 4-5 hours to acquire the necessary data for a single patient slide. These performance numbers do not allow for the high volume of patient slides required to complete the measurements required for both clinical and complex biological studies.

DEFINITIONS

Figure 1:
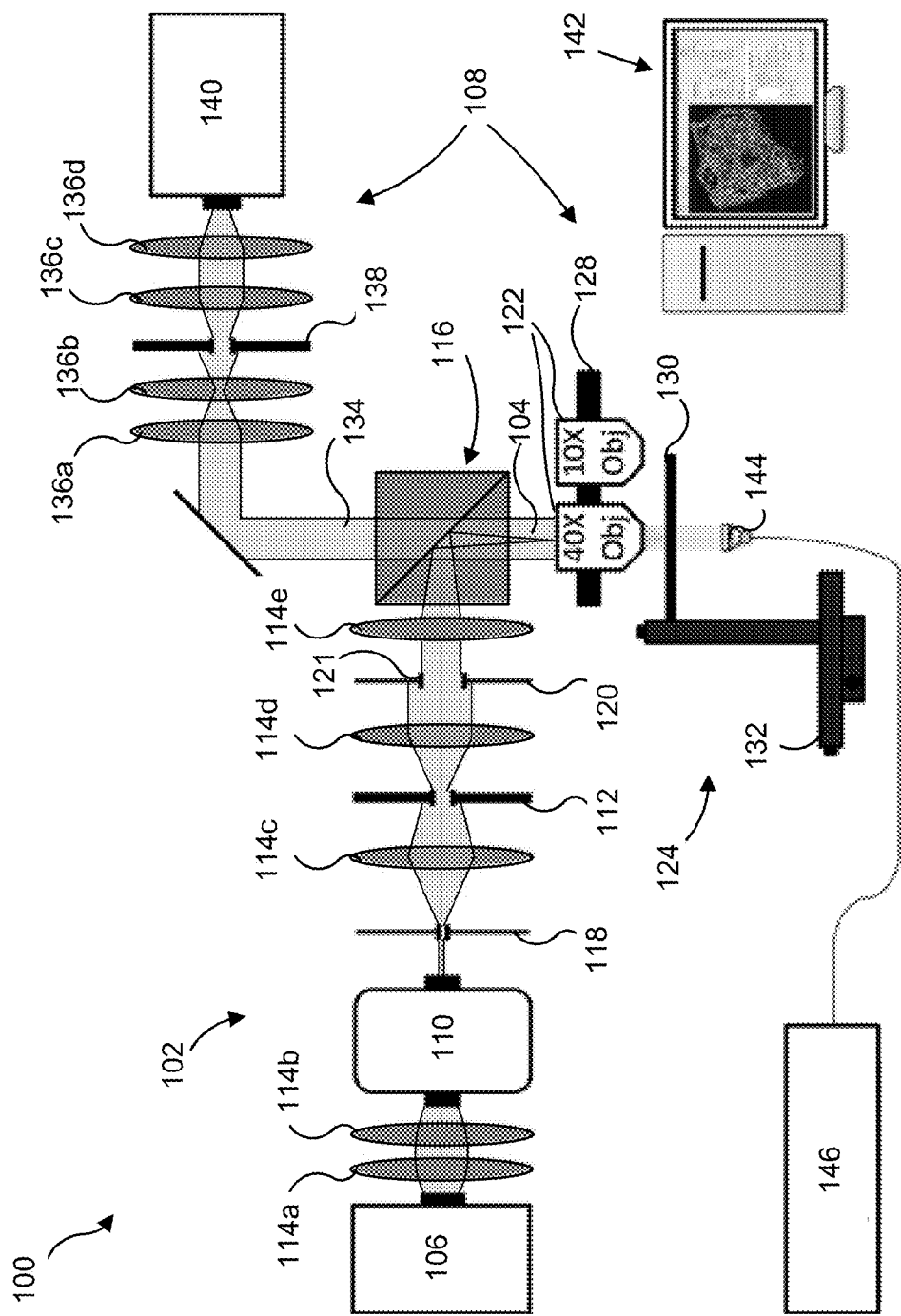
FIG. 1 shows a schematic of a high throughput PWS (HT-PWS) system in accordance with an embodiment of the present technology.

As used herein, the term "automated" refers to a method (e.g., "automated process") in which one or more steps are performed without the need for operator intervention, or to a system or apparatus (e.g., "automated instrument") that performs one or more of its functions without operator intervention.

As used herein, the term "fully automated" refers to a system, apparatus, or method that includes the capability of not requiring an operator for steps following initial set-up, yet is capable of maintaining the quality of the data over a time period unmonitored or unattended by an operator. In particular embodiments, an operator provides a sample to a system or apparatus and/or initiates acquisition, and data and/or analysis is generated without subsequent operator intervention.

As used herein, the term "high throughput" refers to a system, apparatus, or method that allows rapid sample analysis (e.g., analysis of multiple sample simultaneously, back-to-back sample analysis without intervening operator intervention, >2-fold increase in rate of data acquisition over standard analysis (e.g., >5-fold, >10-fold, etc.), etc.).

As used herein, the term "measured autofocusing" refers to traditional techniques for autofocusing. Measured autofocus includes "active autofocusing" techniques in which the distance between the optical system and the object is measured (e.g., by IR, ultrasonically, etc.), and "passive autofocusing" techniques in which correct focus is determined by performing passive analysis of the image that is entering the optical system.

As used herein, the term "predictive autofocusing" refers to methods of autofocus in which an algorithm is used to predict the focus based on a measured focus determined for a different time, location, depth of field, wavelength of light, and/or condition.

DETAILED DESCRIPTION

A. Overview

The present technology provides methods, systems, and apparatuses to achieve high throughput and high speed acquisition of partial wave spectroscopic (PWS) microscopic images. In particular, provided herein are PWS apparatuses and systems capable of rapid acquisition of PWS Microscopic images and clinical, diagnostic, and research applications thereof.

Examples of PWS apparatuses, systems, and methods of use thereof are described, for example, in U.S. Pat. No. 7,667,832; U.S. Pat. No. 7,800,746; U.S. Pat. No. 7,652,772; U.S. Pat. No. 8,131,348; U.S. Pat. App. Pub. No. 2012/0214880; U.S. Pat. App. Pub. No. 2008/0278713; U.S. Pat. App. Pub. No. 2008/0180664; and U.S. Pat. App. Pub. No. 2006/0155178; herein incorporated by reference in their entireties.

In some embodiments, the present technology provides automated (e.g., fully automated) and/or high throughput PWS microscopes. In some embodiments, PWS instruments operate in two or more operation modes, for example, a first low-magnification scanning mode and a second high-magnification data-acquisition mode. In some embodiments, PWS instruments operate in a low-magnification scanning mode to facilitate quick, automated target selection (e.g., to identify the location of cells on a slide). In some embodiments, PWS instruments operate in a high magnification data acquisition mode (e.g., to provide PWS images of target cells). In some embodiments, a PWS instrument performs a first scan of a sample carrier (e.g., microscope slide). For example, the first scan can be a first low magnification scan of the entire sample carrier, or in another embodiment, a scan of a portion of the sample carrier (e.g., at regular intervals, at random locations, etc.) to identify the location of a sample (e.g., cells) on the sample carrier (e.g., slide). In another embodiment, the first scan can be used to capture a transmission or fluorescent image of the sample carrier and/or a portion thereof. Following the first scan, a high-magnification scan for PWS data acquisition can be performed at the locations identified in the first scan. In particular embodiments, by limiting high magnification data acquisition to locations already screened by first scan (e.g., low magnification scan, transmission and/or fluorescent image capture, etc.) of the entire sample carrier, the slower process of high magnification scanning is performed at a limited number of locations, thereby speeding the process. Similarly, by removing operator-selection of locations for high magnification scans, accuracy and precision of data are enhanced, speed of data acquisition is increased, and operator-bias is removed/reduced.

In certain embodiments, PWS instruments and systems, and methods of use thereof reduce the time spent during one or all steps of the acquisition process. In some steps, rate-limiting manual steps (e.g., selection of scan locations) are absent from the processes. In some embodiments, slower process steps (e.g., high magnification data acquisition) are limited to regions of interest (e.g., regions identified by faster low magnification scanning). In some embodiments, complete data acquisition for a single cell takes 20 seconds or less (e.g., <18 seconds, <10 seconds, <9 seconds, <8 seconds, <7 seconds, <6 seconds, <5 seconds, <4 seconds, <3 seconds, <2 seconds, <1 second, etc.). In some embodiments, complete data acquisition (e.g., low magnification scanning mode and high magnification data acquisition mode) for all the measurements on a sample (e.g., single sample slide) is completed in <20 minutes per sample (e.g., <15 minutes, <10 minutes, <9 minutes, <8 minutes, <7 minutes, <6 minutes, <5 minutes, <4 minutes, <3 minutes, <2 minutes, <1 minute, etc.)

In some embodiments, a high throughput PWS apparatus utilizes Köhler illumination, for example, to increase the uniformity of illumination on the sample and/or to increase the spectral sampling speed. In some embodiments, Köhler illumination provides even illumination of the sample, reduces image artifacts, and provides high sample contrast. In some embodiments utilizing Köhler illumination, a PWS instrument comprises one or more (e.g., all) of a collector lens and/or field lens, field diaphragm, condenser diaphragm, and condenser lens. In certain embodiments, an instrument or system comprises components sufficient for, and arranged to achieve, Köhler illumination of a sample.

In some embodiments, a high throughput PWS apparatus utilizes either tunable illumination or tunable acquisition of light reflected from an imaged object, for example, to increase the spectral sampling speed. The tunable illumination can be achieved by any suitable components or arrangement thereof, including the use of an acousto-optic tunable filter, liquid crystal tunable filter, electronically tunable filter, electromechanical optical filter wheel, electro-optical filter; a holographic filter; any other spectral switching method to tune the illumination light across a spectral range (e.g., 10-1000 nm, 300-900 nm, 450-800 nm, etc.), combinations thereof, and combinations with other optical elements. In certain embodiments, a PWS instrument comprises a tunable filter, for example, to provide exposure of a sample to an illumination spectrum over a defined time period (e.g., for data acquisition across a spectrum of wavelengths). In particular embodiments, a tunable filter is an acousto-optic tunable filter or liquid crystal tunable filter. In some embodiments, a selectable wavelength of light is emitted, while others are excluded. In some embodiments, a narrow range of wavelengths (e.g., bandwidth) are emitted at a particular instant (e.g., <10 nm, <5 nm, <2 nm, <1 nm, or less). In some embodiments, a range of wavelengths can be rapidly scanned through (e.g., exposing a sample to a spectrum of wavelengths over time). In some embodiments, the tunable illumination of a PWS instrument is capable of scanning a sample or region of interest thereof (e.g., target cell) through a spectrum of light wavelengths (e.g., 10-1000 nm, 300-900 nm, 450-800 nm, etc.) during the data acquisition time (e.g., <1 minute, <30 seconds, <20 seconds, <10 seconds, <5 seconds, <2 seconds, <1 second). In some embodiments, tunable illumination and the components necessary for achieving such illumination, are under control of a processor and/or controller. In some embodiments, changes in illumination wavelength are accompanied by and/or coordinated with other operations in the system by the processor/controller.

In some embodiments, a high throughput PWS apparatus comprises an electronic motorized aperture to adjust the illumination numerical aperture (NA). In certain embodiments, the numerical aperture of the illumination objective is controlled by imaging the electronic motorized aperture on to the back focal plane of the illumination objective. In another aspect, a motor can change the aperture of the optical imaging system (e.g., by adjusting a motorized aperture within the system). In some embodiments, a motorized aperture is under control of a electronic/computer processor. In certain embodiments, aperture affects the imaging properties of the system (e.g., depth of focus, depth of field, aliasing properties, aberration tolerance, etc.). Accordingly, in some embodiments, a processor directs additional adjustment, e.g., movement of filters, lenses, or other optics to achieve desired optical/spectroscopic properties.

In some embodiments, a high throughput PWS instrument comprises high-speed automated hardware for fast, fully automated data collection. In particular, it contains electronic stages for automated slide scanning and focusing. In addition, the high throughput apparatus contains an automated objective turret to switch between high magnification and low magnification objectives.

In some embodiments, software, code, or other executable instructions are provided to direct and/or control (e.g., along with a controller or processor) automated data collection by a PWS instrument. In some embodiments, automation and/or high-throughput software is incorporated into a high throughput PWS instrument, and provides one or more of: slide intake, sample switching, slide mapping, cell position identification, autofocusing on the sample, etc. In certain embodiments, high throughput software enables performing automated and high throughput PWS measurements.

In some embodiments, one or more of the components of a PWS instrument or system are under the control of one or more electronic controllers or computer processors. In certain embodiments, components and processes that enhance data collection rate and enable automation and/or high-throughput capacity are controlled by a processor. In some embodiments, a processor controls numerous components of a PWS instrument or system and coordinates their actions to achieve the desired/directed function.

In some embodiments, a high throughput PWS instrument or system comprises one or more devices, elements, or components (e.g., auxiliary devices, elements, or components) for collection of non-PWS data and/or acquisition of non-PWS images, in addition to the PWS functionality of the instrument or system. For example, in some embodiments, a transilluminator or transillumination component (e.g., transillumination arm) is provided to allow collection of, for example, bright-field images, dark-field images, fluorescence images, phase contrast images, reflectance spectroscopy, etc.

In some embodiments, the present technology provides methods of selecting target locations on a sample-containing substrate for PWS microscopy that comprises (a) creating a PWS image of the substrate at a first magnification using a PWS system; and (b) selecting target locations on the substrate for PWS microscopy at a second magnification based on the PWS image, wherein the second magnification is higher than the first magnification. In some embodiments, the first magnification is between 2× and 20×. In some embodiments, the second magnification is between 20× and 200×. In some embodiments, the PWS image is of all or a portion of the substrate. In some embodiments, the substrate is a microscopy slide. In some embodiments, the sample comprises cells. In some embodiments, the target locations comprise one or more cells with target-cell characteristics. In some embodiments, target-cell characteristics are selected from the group consisting of size, morphology, positioning on the slide, and spacing between cells. In some embodiments, the selecting is performed manually by a user. In some embodiments, the selecting is performed automatically by a selection algorithm. In some embodiments, the step of creating a PWS image of the substrate at a first magnification can include (i) collecting multiple PWS images of the substrate at the first magnification; and (ii) tiling the multiple images together to create a single larger image of the substrate. In some embodiments, steps (i) and (ii) are performed automatically by the PWS instrument. In some embodiments, the PWS images of the substrate at the first magnification are obtained using any suitable optical technique such as, for example, fluorescent, bright-field, dark-field, phase contrast, reflectance, etc. In some embodiments, methods can further comprise a step prior to step (a) of calculating the number of images required to map a region of the substrate based on a pixels-to-micron conversion factor specific to the PWS instrument. In some embodiments, the pixels-to-micron conversion factor is dependent upon an objective lens and imaging sensor of the PWS instrument. In some embodiments, during the collecting of multiple PWS images of the substrate at the first magnification, measured autofocusing is performed before a first PWS image is collected, a predictive autofocusing algorithm is used prior to a number of subsequent PWS images, and measured autofocusing is periodically repeated with the predictive autofocusing algorithm used between instances of measured autofocusing. In some embodiments, measured autofocusing is repeated every 2-50 images (e.g., 15 images, 30 images, 45 images, etc.).

In some embodiments, the present technology provides methods of analyzing a sample by high-throughput partial wave spectroscopy (PWS) microscopy that comprise (a) selecting target locations on a sample-containing substrate by methods as described herein; and (b) obtaining PWS measurements of the target locations at the second magnification. In some embodiments, obtaining PWS measurements can include automatically (i) centering the system on a first of the target locations; (ii) autofocusing on the first of the target locations; (iii) spectrally scanning the first of the target locations at a range of illumination wavelengths; and (iv) collecting a PWS image at each illumination wavelength. In some embodiments, steps (iii) and (iv) comprise illuminating a target location with a wavelength of light and collecting a PWS image for each stepwise wavelength in the range of illumination wavelengths. In some embodiments, the range of illumination wavelengths comprises all or a portion of the human visible spectrum (e.g., 462-700 nm). In some embodiments, each stepwise wavelength comprises a step size of 1-10 nm (e.g., 2 nm) In some embodiments, methods can further comprise (v) repeating steps (i)-(iv) for additional target locations.

In some embodiments, the present technology provides partial wave spectroscopy (PWS) systems that comprise tunable Köhler illumination to provide a broad spectrum of incident light on a target; and a receiving end positioned in an imaging plane of the system to separately record intensity of multiple spectra of backscattered light from one or more preselected areas of the target illuminated with the incident light, the multiple spectra of emergent light resulting from refractive index fluctuations within the target. In some embodiments, light from a light source is focused through an acousto-optic tunable filter. In some embodiments, light exiting from the acousto-optic tunable filter is then focused through an electronic motorized aperture that sets the illumination numerical aperture. In some embodiments, light exiting the electronic motorized aperture is collimated, passed through a field aperture, and focused onto a back focal plane of an objective lens. In some embodiments, systems can further comprise components for automated high throughput PWS, such as for example, an automated stage, an automated objective turret, a second motorized aperture to control the angle of the collected backscattered light, and hardware triggers between the acousto-optic tunable filter and the receiving end to synchronization wavelength tuning and image capture. In some embodiments, the light source comprises a xenon lamp. In some embodiments, the receiving end comprises an imaging spectrograph capable of receiving at least two distinct spectra within the broad spectrum of incident light. In some embodiments, the illumination source provides, and the receiving end receives, light comprising the human-visible spectrum. In some embodiments, systems further comprise a light detector coupled with an imaging spectrograph, and a scanning stage coupled with the imaging spectrograph and the light detector, the scanning stage operatively configured to move about a predetermined position. In some embodiments, the light detector is a charge-coupled device (CCD) camera. In some embodiments, the light detector is a plurality of photodetectors. In a particular example, the light detector can be a chemical detection camera configured to detect light (e.g., in the range from ultraviolet to the near infrared), such as the Arrow™ (available from Rebellion Photonics Inc. of 7547 S. FWY., Houston Tex. 77021). In some embodiments, the target comprises one or more living cells of a biological sample with a thickness less than the mean free path of light in the sample. In some embodiments, the receiving end further comprises one or more single channel linear-array spectrometers. In some embodiments, the one or more preselected areas of the target are microscopic. In some embodiments, the incident light is configured to propagate through the microscopic target in substantially one dimension. In some embodiments, methods further comprise one or more optical components operatively configured to focus the incident light on the microscopic target. In some embodiments, systems further comprise one or more optical components operatively configured to magnify the light emerging from the microscopic target for recordation by the receiving end. In some embodiments, the receiving end records spectral information on a cell by cell basis.

In some embodiments, the present technology provides methods of collecting a partial wave spectroscopy x/y/λ-data cube of a target that include focusing the system on an x/y target location, and spectrally scanning the target location while collecting an x/y image at each illumination wavelength of the spectral scan. In some embodiments, spectrally scanning comprises illuminating the x/y target locations at series of illumination wavelengths throughout a spectrum and collecting an image at each wavelength. In some embodiments, the spectrum comprises a portion of the human-visible spectrum. In some embodiments, the spectrum comprises 462-700 nm. In some embodiments, the series of illumination wavelengths are 1-10 nm steps. In some embodiments, the series of illumination wavelengths are 2 nm steps. In other embodiments, the steps can be greater than 10 nm steps (e.g., with use of a chemical detection camera). In some embodiments, the x/y target location comprises a cell. In some embodiments, the x/y image is the result of collected backscattered light from backscattered light from the x/y target location illuminated at a single wavelength.

In some embodiments, the present technology provides PWS systems configured to collect PWS data at two or more magnification levels comprising an objective turret equipped with two or more objective lenses of different magnifications, the objective turret being movable between at least first and second positions, the first position placing a low magnification objective lens in the path between a light source and a target location, and the second position placing a high magnification objective lens in the path between a light source and a target location. In some embodiments, low magnification is less than 20× and high magnification is greater than 20×.

B. Selected Embodiments of HT-PWS Systems and Methods

The present technology provides methods, systems, and apparatuses to achieve high throughput and high speed acquisition of partial wave spectroscopic (PWS) microscopic images. In particular, provided herein are PWS apparatuses and systems capable of rapid acquisition of PWS microscopic images and clinical, diagnostic, and research applications thereof.

Various aspects of the present technology are directed to high-throughput partial wave spectroscopy (HT-PWS) as a high-speed spectral nanocytology technique that analyzes the field effect of biological samples (e.g., cells, cancer cells, etc.) to provide diagnostic and other cell screening information in a non-invasive manner. In particular examples, an HT-PWS system as disclosed herein, includes automated hardware and an acousto-optic tunable filter to scan sample slides at low magnification in a manner that allows rapid selection of target positions (e.g., selection of specific target cells on the sample slides). Following a low magnification slide mapping process, spectra at each spatial pixel in a cell between, for example, about 400 nm and about 800 nm (e.g., about 450 nm to about 700 nm), can be rapidly acquired (e.g., 30 cells can be measured in about 40 minutes) for PWS measurement. In various embodiments, statistical quantitative analysis on the size and density of intracellular nanostructures can be extracted from the spectra at each pixel in a cell, for example, to yield a diagnostic biomarker such as disorder strength ($L_d$) that can be used to diagnose and/or detect significant differences in intracellular nanostructure. In one embodiment, the HT-PWS system can be used for the detection of or diagnosis of cancerous cells in a patient cell sample by comparing differences in diagnostic biomarker, $L_d$.

FIG. 1 shows a schematic of a high throughput PWS (HT-PWS) system 100 ("system 100") including a HT-PWS instrument arrangement in accordance with one embodiment of the present technology. As shown in FIG. 1, the system 100 includes an illumination system 102 for providing a broad spectrum of incident light 104 from a light source 106 on a target sample (not shown), and includes a receiving end 108 positioned in an imaging plane of the system 100 and configured to record intensity of multiple spectra of backscattered light from the target sample illuminated with the incident light 104. In one embodiment, the illumination system 102 can incorporate tunable illumination which is incident on a sample (not shown) from a tunable filter 110, such as an acousto-optic tunable filter. The illumination system 102 can also include a first electronic aperture 112 that can adjustably set an illumination numerical aperture (NA). The illumination system 102 further includes a plurality of lenses 114 (individually identified as 114a-114e) that can function as collecting lenses, collimating lenses, both collecting and collimating lenses and/or other lenses (e.g., imaging lenses, condenser lenses, etc.) that the light 104 is passed through from the light source 106 to the receiving end 108 via a beamsplitter 116.

In some embodiments, the illumination system 102 can be a Köhler illumination system and/or achieve Köhler illumination of a sample, target, and/or target location. Aspects of the present technology can include any suitable configuration of components for achieving Köhler illumination. In one embodiment, light is gathered from the light source 106 (e.g., a xenon lamp or other broadband light source) by a series of lenses 114 (e.g., collecting lens 114a and collimating lens 114b), passes through a high temperature aperture 118, a first imaging lens 114c, the first electronic aperture 112, a second imaging lens 114d, and then passes through a field stop diaphragm 120 located at the focal plane of a condenser lens 114e so that an object being examined (e.g., target sample) is imaged in the plane of the diaphragm 120. In this arrangement, adjustment of the field stop diaphragm aperture 121, permits the illuminated areas to be adjusted to the size of the object. In this arrangement, the field stop diaphragm 120 located at the focal plane of the condenser lens 114e permits the amount and angularity of the light to be adjusted. Additionally, adjustment of the diaphragm aperture's A-stop can provide control of the angle of light passing through the aperture 121, which can increase sensitivity and/or provide higher resolution in the HT-PWS system 100. Further, arranging the condenser lens 114e proximate to the target object directs the light 104 so that all of the light 104 transmitted from each point in the light source 106 emerges from the condenser lens 114e as a bundle of parallel rays of such a size as to illuminate the entire target object from a direction corresponding to the location of the point in the light source 106 which is considered. One aspect of using the Köhler arrangement is that the target object has uniform illumination across the entire field of view, with both axial light and angular light from every direction. Other components, and arrangements thereof, for achieving such illumination are also contemplated.

In some embodiments, PWS instruments comprise (or PWS methods utilize) a tunable illumination system and/or achieve tunable illumination of a sample, target, and/or target location. Aspects of the present technology can include any suitable configuration of components (e.g., filter(s)) for achieving tunable illumination. In one embodiment and as shown in FIG. 1, light from the light source 106 is passed through a tunable filter 110 to provide light at a specific wavelength or a wavelength range of a particular bandwidth (e.g., selectable bandwidth) to downstream optics, components, sample, target, etc. In some embodiments, the illumination system 102 comprises a tunable bandpass filter, acousto-optic tunable filter (AOTF) 110, liquid crystal tunable filter, or other component suitable for receiving a spectrum of light and outputting a selected (e.g., tunable) wavelength or set of wavelengths. In certain embodiments, a component is capable of rapidly switching (e.g., stepping) through wavelengths (e.g., <200 µs, <100 µs, <75 µs, <50 µs, <25 µs, etc.). In some embodiments, a component is capable of accurately (e.g., having an error of: ±<0.1 nm, ±<0.05 nm, ±<0.01 nm, ±<0.005 nm, ±<0.001 nm, etc.) switching between wavelengths at steps of 0.1 nm, 0.2 nm, 0.5 nm, 1 nm, 2 nm, 3 nm, 4 nm, 5 nm, 6 nm, 7 nm, 8 nm, 9 nm, 10 nm, etc.

In additional embodiments, a HT-PWS system 100 can include a Köhler illumination alignment/arrangement with tunable illumination, for example, to increase uniformity of illumination and spectral sampling speed. For example, in one embodiment, light from the light source 106 (e.g., xenon lamp) is focused through a tunable filter 110 (e.g., an acousto-optic tunable filter). In one particular embodiment, the light source 106 can be a xenon lamp from Oriel® Instruments of 150 Long Beach Blvd., Stratford, Conn. 06615. In other embodiments, the light source 106 can include any broadband light source and, for example, a long-life laser activated xenon source. In another particular embodiment, the tunable filter 110 can be an acousto-optic tunable filter (AOTF) from Gooch & Housego PLC of Dowlish Ford, Ilminster, TA19 OPF, United Kingdom. In other embodiments, the AOTF can be a separate module of the HT-PWS system 100 that can be incorporated into a conventional microscope for performing HT-PWS measurements of samples. In some embodiments, the AOTF has a minimum switching speed of less than 100 µs (e.g. 50 µs or less), bandwidth of less than 10 nm (e.g., 5 nm, 4 nm, 3 nm, 2 nm, 1 nm, or less), and a spectral range encompassing all or a portion of the human visible spectrum (e.g., 462-700 nm). The tuned light exiting the AOTF can then be focused through a first electronic motorized aperture 112 (e.g., such as available from Newport Corp. of 1791 Deere Ave., Irvine, Calif. 92606) that sets the illumination numerical aperture (NA). Light exiting the first electronic motorized aperture 112 can then be collimated and passed through a field aperture 120 (e.g., a field stop diaphragm) after which it is focused onto the back focal plane of an objective lens 122 (e.g., Olympus 40× objective lens (NA=0.6) from Olympus America of 3500 Corporate Pkwy, Center Valley, Pa. 18034).

In some embodiments, illumination schemes described herein achieve illumination of uniform intensity due to the Köhler alignment and wavelength switching in less than 100 µs. Further, in embodiments in which the incident illumination is of a single wavelength, the illumination system allows fluorescence experiments and molecular specific dye experiments to be performed.

Referring back to FIG. 1, the HT-PWS system 100 also includes the receiving end 108, which is positioned in the imaging plane of the system 100 and configured to record intensity of multiple spectra of the backscattered light from the target sample illuminated with the incident light 104 provided by the illumination system 102 as discussed above. In some embodiments, the receiving end 108 can include a scanning stage 124 for supporting the target sample and an imaging spectrograph 126 configured to receive at least two distinct spectra within a broad spectrum of incident light. The receiving end 108 can further include an objective turret 128 for supporting and positioning one or more objective lenses 122 in the light path.

In some embodiments, the HT-PWS system can include high-speed automated hardware. In some embodiments, such hardware and systems facilitate fast, fully automated PWS data collection. For example, in some embodiments, the HT-PWS receiving end 108 can comprise the scanning stage 124, such as an automated, encoded, linear stage (e.g., Zaber Technologies) for the x, y and/or z-axes. In certain embodiments, the HT-PWS system can include an automated objective turret 128. In some embodiments, an automated objective turret 128 allows automated switching between a high-magnification objective lens (e.g., 200×, 150×, 100×, 80×, 50×, 40×, 30×, 25×, etc.) and low-magnification objective lens (15×, 10×, 5×, 2×, etc.).

In other embodiments, the receiving end 108 comprises a motion system (not shown) that allows for movement of a sample relative to the other components (e.g., optics) of the system 100, the optics of the system 100 relative to the sample, or a combination thereof. The motion system can allow the HT-PWS system 100 to center or focus on the appropriate portion of the sample (e.g., target location). In particular embodiments, a motion system can provide movement along the x-axis, y-axis, and/or z-axis, such that the scanning stage 124 can operatively move about a predetermined position. In some embodiments, a motion system includes the scanning stage 124 (e.g., a linear stage, FIG. 1)

that provides translational movement along a single axis (e.g., x-axis, y-axis, z-axis). An example of a scanning stage 124 includes a platform element 130 and a base element 132, joined by a guide or linear bearing, such that the movement of the platform element 130 with respect to the base element 132 is restricted to translational motion along a single axis (e.g., x, y, z). In some embodiments, a guide allows movement via any suitable mechanism including, but not limited to, ball bearings, recirculating ball bearings, crossed roller ball, flexure, cylindrical sleeve, dovetail, etc. In some embodiments, movement along the guide is supplied by a linear actuator (e.g., motorize, pneumatic, hydraulic, Piezo, etc.). In particular embodiments, the motion system can include a multi-axis stage configuration in which multiple linear stages (e.g. 2, 3) allow for translational movement in multiple directions. For example, a multi-axis stage configuration can include three linear stages mounted orthogonally to each other to allow for movement of the sample along the x-axis, y-axis, and z-axis with respect to the remaining or stationary HT-PWS instrumentation. In some embodiments, movement of one or more (e.g., all) of the scanning stages is automated. In other embodiments, movement is controlled and/or directed by a processor within or in communication with the HT-PWS system 100. In some embodiments, movement is synchronized with other actions of the HT-PWS system 100. In various embodiments, the motion system is encoded. For example, a scale (not shown) can be incorporated into the motion system and an encoder (not shown) can be used to measure the position relative to the scale and report this to the controller or processor directing the movement. An encoded stage allows a motion controller to reliably and repeatable move the stage to set positions.

As discussed herein and in some embodiments, the HT-PWS instrument can be configured for data collection at two or more different magnification levels. For example, the HT-PWS system 100 can be configured for data collection at >20× (e.g., 40×), or in another embodiment, at <20× (e.g., 10×). In particular embodiments, multiple magnification levels, and switching between multiple magnifications, can be achieved by the objective turret 128. In some embodiments, the objective turret 128 includes two or more objective lenses 122 (e.g., 2, 3, 4, 5, 6, 7, 8, etc.) of differing magnification levels. In some embodiments, movement of the turret 128 (e.g., rotation, translation, etc.) from one position to another position switches the objective lens 122 utilized by the HT-PWS system 100 for data collection, and thereby changes the magnification at which data is collected by the imaging spectrograph 126. As discussed above, the objective turret 128 can be automated. For example, an automated objective turret 128 can be driven by an actuator or other motor, and movement thereof is controlled and/or directed by a processor within or in communication with the HT-PWS system 100.

The imaging spectrograph 126 can be configured to receive two or more distinct spectra within a broad spectrum (e.g., human visible spectrum) of incident light. In certain embodiments, backscattered light 134 can be collected through a plurality of lenses 136 (individually identified as 136a-136d) that can function as collecting lenses, collimating lenses, both collecting and collimating lenses and/or other lenses (e.g., imaging lenses, condenser lenses, etc.) that the light 134 is passed through to a second electronic aperture 138 that sets the collection numerical aperture (NA) and a light detector 140. In certain embodiments, the second electronic aperture 138 (e.g., such as available from Newport Corporation of 1791 Deere Ave., Irvine, Calif. 92606) provides control of the low angle of the collected backscattered light 134. In some embodiments, the light 134 is focused on the light detector 140. In one embodiment, the light detector 140 is a high-speed complementary metal-oxide-semiconductor (CMOS) camera. In one embodiment, the imaging spectrograph 126 can include an ultra-fast CMOS camera (e.g., such as ORCA-Flash 4.0 available from Hamamatsu Photonics K. K. of 325-6, Sunayama-cho, Naka-ku, Hamamatsu City, Shizuoka Pref., 430-8587, Japan). In another embodiment, the light detector 140 is a CCD camera. In some embodiments, the light detector 140 is a plurality of photodetectors. In a particular example, the light detector 140 can be a chemical detection camera configured to detect light (e.g., in the range from ultraviolet to the near infrared), such as the Arrow™ (available from Rebellion Photonics Inc. of 7547 S. FWY., Houston Tex. 77021). Data collection can be automated via an acquisition graphical user interface (GUI) 142 (e.g., for acquiring data in real-time). In certain embodiments, the HT-PWS system 100 can also incorporate transmission bright-field image collection with a fiber collimator 144 for transmission illumination and a fiber-coupled source 146 (e.g., a white LED fiber coupled source).

In some embodiments, the components (e.g., optics) of the HT-PWS system 100 comprises one or more apertures. For example, an illumination aperture (e.g., the first electronic aperture 112) can set the illumination NA and a collection aperture (e.g., the second electronic aperture 138 can set the collection NA. In some embodiments, one or more apertures are automated, electronic, and/or motorized apertures. In such embodiments, the diameter of an aperture and/or the numerical aperture (NA) is set and/or altered under the control and/or direction of a controller or processor (not shown) within or in communication with the HT-PWS system 100. In some embodiments, the size of the aperture is synchronized with other actions of the HT-PWS system 100. Automation of an aperture allows the HT-PWS system 100 to switch between modes, and or move through a scan rapidly and without user intervention. In various embodiments, the illumination NA and the collection NA can be set independent of each other. In another embodiment, the illumination NA can be optimally set for illumination a particular target sample size, thickness and/or density. In further embodiments, the collection NA can be optimally set for collecting the backscattered light 134 and sharpening the image produced from the target sample. In one embodiment, the first electronic aperture 112 can set a low illumination NA so as to reduce the angle of the incident light 104 emitted from the illumination system 102. In another embodiment, the second electronic aperture 138 can set a high collection NA so as to sharpen (e.g., reduce blurriness) the PWS image generated by the system 100.

In some embodiments, coupling and/or synchronization of steps enhances the automation and speed of the process of obtaining PWS and/or other data. For example, synchronization of wavelength tuning and image capture, for example via hardware triggers (e.g., between the AOTF and the camera), enhances a data acquisition rate. In some embodiments, sensitivity and exposure time can be minimized via binning of data (e.g., 2×2 binning). In certain embodiments, binning (e.g., 2×2 binning) is enabled by the camera to enhance data acquisition speed.

In addition to PWS illumination, certain embodiments include a transmission illumination element (e.g., transillumination arm) that can facilitate collection of bright-field, dark-field, fluorescence, polarized and/or phase contrast images in addition to PWS measurements. Accordingly, in various embodiments, images generated by bright-field, dark-field, fluorescence, polarized and/or phase contrast illumination can be used to select sample targets (e.g., preselect cells) for PWS analysis. In some embodiments, a white-LED fiber-coupled source 146 (e.g., such as available from WT&T of 277 Lakeshore Rd., Suite #04, Pointe Claire, Quebec, H9S 4L2, Canada) can be connected to a fiber collimator 144 and the output beam can be passed through a diffuser. The transmitted light can then be collected via a high-resolution scientific color camera, such as a high resolution CMOS USB Camera available from Thorlabs Inc. of 56 Sparta Ave., Newton, N.J. 07860 (product number DCC1645C), for generation of non-PWS images. In some embodiments, a high-resolution scientific color camera also allows for rapid collection of low-magnification/low-resolution transmission images for slide-mapping. In some embodiments, a flipper mirror can be used to switch between the transmission collection camera and the camera used for PWS measurements.

The instruments and systems of the present technology enable rapid, high throughput, and/or automated PWS data collection. The benefits of these instruments, systems, and/or combination of components are not limited to any particular application. In some embodiments, any combination of components of a PWS instrument or system may be utilized to achieve a desired function or process. In particular embodiments, PWS instruments and systems provide a procedure for high throughput sample analysis, wherein a sample is rapidly analyzed by low magnification PWS to identify targets or potential targets (e.g., cells, cells with potential nanoarchitectural abnormalities, potentially cancerous cells, etc.), followed by slower, high magnification PWS of the identified targets. Such embodiments allow high resolution data to be acquired of targets in a suitable timeframe for research and/or clinical use. In some embodiments, transmission or fluorescent images can be first acquired at low magnification to identify targets or potential targets. Once targets are identified, high magnification objective lenses can be used to for acquiring high resolution PWS data at the selected targeted sites (e.g., cells). In further embodiments, dark field illuminated samples can be used to acquire high resolution spectral (PWS) data from selected targeted sites (e.g., cells).

In accordance with aspects of the present technology, data acquisition time is expended acquiring high resolution images of targets of interest (e.g., cells, potentially cancerous cells, etc.), while resources are not wasted obtaining such detailed data on regions of a sample with less potential for revealing useful information (e.g., regions lacking cells, regions lacking the appropriate type of cells, etc.). Although data acquisition can be focused on selected sample targets or cells, the use of high throughput PWS instruments and systems are not limited to such applications.

In a two-mode sample analysis (e.g., target identification mode and data acquisition mode), the first task can include generating a large low-magnification (e.g., 5×, 10×, etc.) image of the sample (e.g., sample-containing substrate (e.g., slide). In some embodiments, this is accomplished by an algorithm which rapidly collects many low-resolution images and tiles them together to create the full image of the slide. A user may specify the bounds of the region to be mapped (e.g., by specifying the positions of diagonal corners), or preset bounds may be used. An algorithm then calculates the number of images required to map the entire region specified based on a pixels-to-micron-conversion factor specific to the objective lens and the camera imaging sensor used. The region can then be scanned in a raster pattern and an image is acquired at each x and y position necessary to make a complete image of the region (e.g., without holes or overlaps). In such embodiments, all the images can then be tiled together to form a complete image of the entire region (e.g., as specified by the user).

In some embodiments, the speed of automated slide mapping can be maximized by autofocusing (e.g., using measured autofocusing techniques) only on the first image. In some embodiments, a predictive autofocusing method can be used for subsequent images. In certain embodiments, the focus can be rechecked and/or corrected as necessary (or as specified by the user or as a pre-set parameter) throughout or during the scan. For example, the focus can be checked via measured autofocusing techniques and/or corrected at intervals such as every 10 images, every 20 images, every 30 images, every 40 images, every 50 images, every 100 images, every 1 minute interval, every 2 minutes, every 5 minutes, etc.). The captured images can be stored and tiled together (e.g., in real-time or after completion of the scan). In various embodiments, the images can be stored on memory internal to the PWS instrument, on an external hard drive or other memory unit, or on a computer in communication (e.g., wireless or hard wired) with the PWS instrument. In some embodiments, individual images or sets of images (a consecutive line of images, a complete set of images, tiled compilation of images, etc.) can be stored on and transferred to/from various memory units without affecting the speed of data acquisition. In some embodiments, images can be stored on computer memory until the end of each capture session before being saved to a hard disk. In this embodiment, the data acquisition algorithm can avoid overloading the computer's physical memory.

Following low resolution image acquisition and tiling to generate an image of the selected area (e.g., entire sample slide, portion of sample slide containing biological matter, etc.), target identification is performed (e.g., automated target identification by the PWS instrument). In some embodiments, identifying targets, such as selecting specific cells or nanoarchitecture of cells, for more detailed imaging can include reviewing the low-magnification image for regions or positions of interest. In particular embodiments, target selection is performed from the large low-magnification image of the slide generated by a slide-mapping algorithm. In some embodiments, target selection is performed using image-segmentation and cell-identification algorithms (or a single algorithm that performs both functions). In particular embodiments, cell-identification algorithms can be unique for the cell type being analyzed. For example, in the case of buccal PWS, a cell-identification algorithm will identify cells that are isolated, non-overlapping and with size greater than 60 µm. In other embodiments, a cell identification algorithm, for buccal PWS or other applications, will use different criteria (e.g., size, degree of separation, morphology, etc.) entered by a user or from a pre-set criteria list. In some embodiments, a master cell-identification algorithm allows selection of different cell types.

In some embodiments, a cell-identification algorithm generates a list of candidate locations (e.g., cells) from which the targets for the data acquisition phase are to be selected. In some embodiments, images of each potential target cell and its local surroundings are displayed, reported, and/or communicated to the user or a third party (e.g., researcher, clinician, etc.). Such communications can be via a user interface (UI) or a computer or other device (e.g., handheld device) that is in communication with the PWS instrument (e.g., wireless or hard connection). Other examples of such communications can include email and/or printed reports. In some embodiments, a prompt (e.g., on the UI or elsewhere) will query the operator or third party whether to accept the position as a target location or to reject the position for further inquiry (e.g., PWS data collection). In some embodiments, validation of candidate targets is performed automatically (e.g., by a validation algorithm). In some embodiments, a validation algorithm applies criteria to the candidate cells that are distinct from the cell-identification algorithm. In some embodiments, the criteria can vary based on the number of candidate target locations are available. For example, a higher criteria threshold can be applied to samples having a greater number of target candidates. In some embodiments, all positions identified by the cell-identification algorithm are accepted as targets. In certain embodiments, regardless of how candidate positions are validated, each selected target location is saved to a position list (i.e., a target location list). In some embodiments, the position list is utilized in a data acquisition phase. In some embodiments, the position list is exported (e.g., to the Acquisition GUI, an acquisition processor, a memory unit that is accessed during the acquisition mode, etc.).

In certain embodiments, autofocus is provided (e.g., rapid autofocus). Autofocus, such as rapid autofocus, can be included in one or both of automated slide mapping and/or automated PWS measurements (e.g., PWS data acquisition). In one example, a rapid autofocus algorithm is provided that accurately identifies the correct focus plane at any position on the slide. In some embodiments, the autofocus algorithm can contain a two-step process. In these embodiments, the autofocus algorithm can accommodate the higher speed criteria for slide mapping, and can also accommodate the greater accuracy criteria for PWS measurements. In certain embodiments, the first step of an algorithm can be a predictive autofocus algorithm based on the equation of a plane in three dimensions. Three in-focus x, y, z positions on the slide are collected to generate an equation for a plane that predicts the in-focus position anywhere on the slide. Between points where autofocusing (e.g., via measured autofocusing techniques) is actually performed, the predictive autofocus algorithm is used to predict the in-focus z-position during slide mapping. Thus, based on the equation of a plane, the predicted z-position is given by Equation 1 (below), where a, b, c, and d are constants defining the equation of the plane in 3D space and x, y, and z are spatial coordinates.

$$z = \frac{(d - ax - by)}{c} \quad \text{Equation 1}$$

In some embodiments, to more accurately capture an in-focus image at a cell position for PWS measurements, an algorithm based on computing the contrast variance for the entire image can be employed. In one embodiment, the chosen focal position is determined by the highest value of the contrast variance.

In a particular embodiment, to find an in-focus image, the algorithm can search for the z-position that corresponds to the maximum of the contrast variance. In operation, the algorithm scans a user-determined range around the predicted focus position with large incremental steps (~5 µJm). The contrast variance forms a Gaussian shape when plotted, and is centered at the in-focus position. The algorithm detects when the value of the contrast variance switches from increasing to decreasing and stops scanning. The stage then backtracks in fine increments (e.g., ~0.3 µm) to find the maximum of the contrast-variance curve.

In another embodiment, an in-focus image at a selected target position (e.g., a position of a cell of interest), can be acquired by HT-PWS measurement using an algorithm based on edge detection of the field aperture. In one example, the desired focus can be determined by the highest number of edges detected at the edge of the field. In this manner, focus consistency, which is desirable to prevent variability in quantitative HT-PWS $L_d$ analysis, is obtained by focusing on a fixed object that is always in the same position. As such, edges corresponding to the aperture are isolated by segmenting the field-of-view and by applying a black/white threshold to a Sobel gradient magnitude image of the field. In this example, a slight erosion of the segmented field leaves a mask that can be applied to images to obtain only edges corresponding to the field aperture. Accordingly, the algorithm searches for the z-position that corresponds to the maximum number of edges from the field aperture.

Figure 2:
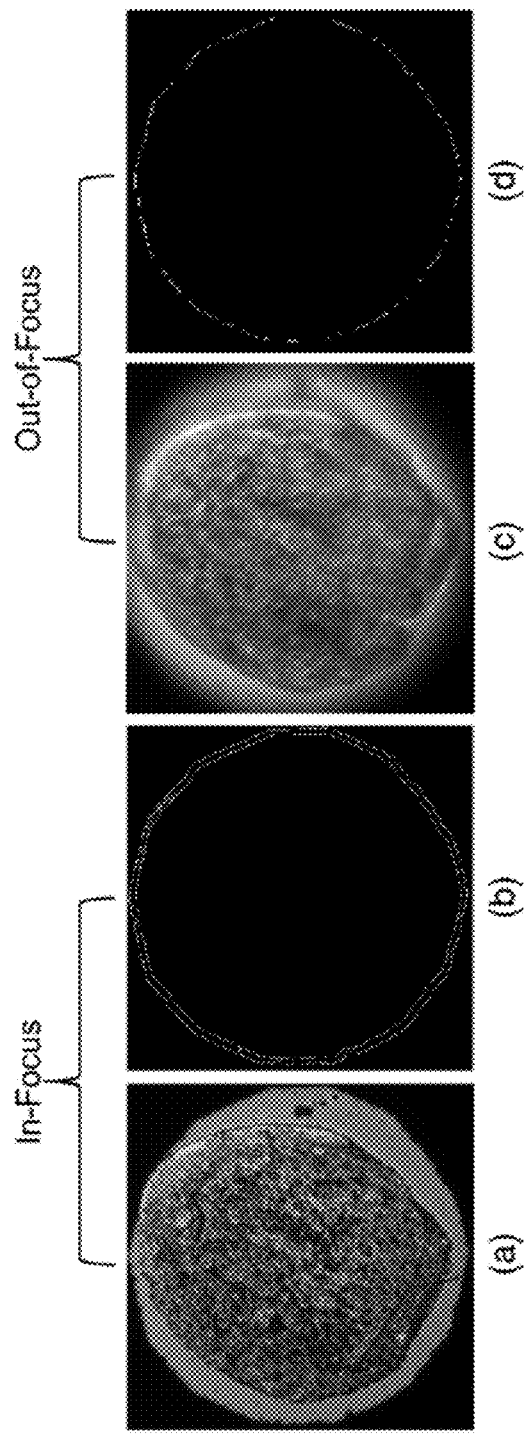
FIGS. 2a-2d illustrate the difference in edges detected for in-focus and out-of-focus images in accordance with an embodiment of the present technology.

In one example, the algorithm can scan a user-determined range around the predicted focus position with incremental steps (e.g., approximately 5 µm). At each position, the number of edges can be found using a Sobel edge detector. The number edges forms a Gaussian curve with the in-focus position corresponding to the center of the peak and the algorithm detects when the number of edges switches from increasing to decreasing and can stop scanning. The stage of the HT-PWS system can backtrack in fine increments (e.g., approximately 0.3 µm) in order to find the maximum number of edges corresponding to the aperture at the current x, y coordinate. FIGS. 2a-2d illustrate the difference in edges detected at the field aperture outside the mask for in-focus and out-of-focus images in accordance with an embodiment of the present technology. For example, FIG. 2a is an in-focus image of buccal cell, and FIG. 2b is a correspond edge map for the in-focus image of FIG. 2a showing the field aperture edges visible outside the border of the mask applied to remove the field. FIG. 2c is an out-of-focus image of the same buccal cell shown in FIG. 2a, and FIG. 2d is a corresponding edge map for the out-of-focus image showing no edges detected outside the border of the mask.

In some embodiments, PWS measurements are obtained from a High Throughput PWS microscope via a user interface (e.g., the PWS GUI, a specialized automated measurement and analysis interface, etc.). In one embodiment, the user interface is the same interface on the PWS instrument used for target identification. In some embodiments, parameters for data acquisition, such as selected positions determined during target identification phase and user parameters (e.g., wavelengths to scan, illumination bandwidth, exposure time, input NA, collection NA, etc.), are automatically loaded, downloaded and/or transferred from a server or other memory storage component. In some embodiments, all parameters can be determined before a target identification phase. In these embodiments, user input and/or intervention would not be necessary between target identification and data acquisition phases. In some embodiments, parameters for target identification and PWS data acquisition can be entered and/or specified separately. For example, a user can enter target identification parameters before the target identification phase and enter data acquisition parameters before the data acquisition phase (e.g., after the target identification phase). In particular examples, settings for a high throughput data acquisition scan include a spectral range with a low parameter being greater than 350 nm (e.g., 360 nm, 370 nm, 380 nm, 390 nm, 400 nm, 410 nm, 420 nm, 430 nm, 440 nm, 450 nm, 460 nm, 470 nm, 480 nm, 490 nm, 500 nm, 510 nm, 520 nm, 530 nm, 540 nm, 550 nm, etc.), a high parameter being lower than 800 nm (e.g., 600 nm, 610 nm, 620 nm, 630 nm, 640 nm, 650 nm, 660 nm, 670 nm, 680 nm, 690 nm, 700 nm, 710 nm, 720 nm, 730 nm, 740 nm, 750 nm, 760 nm, 770 nm, 780 nm, 790 nm, etc.) and with a step size of 0.1-5 nm (e.g., 0.1 nm, 0.2 nm, 0.5 nm, 1.0 nm, 2.0 nm, 3.0 nm, 5.0 nm, etc.). Examples of spectral ranges and step sizes include, but are not limited to, 400 nm-800 nm, 400 nm-750 nm, 430 nm-720 nm, 462 nm-700 nm, etc. with a step size of 1 nm, 2 nm, 3 nm, etc. In some embodiments, input NA is set with the input aperture at 0.5 mm (NA=0.05%), approximating plane wave illumination without sacrificing more light than necessary. In other embodiments, input aperture can be about 10 mm to about 1 mm (e.g., 1 mm, 2 mm, 3 mm, 4 mm, 5 mm, 6 mm, 7 mm, 8 mm, 9 mm, 10 mm, and values therein). In some embodiments, output NA is not constrained by the electronic aperture and is instead determined by the objective lens. For example, NA can be about 0.1 mm to about 1.0 mm (e.g., 0.1 mm, 0.2 mm, 0.3 mm, 0.4 mm, 0.5 mm, 0.6 mm, 0.7 mm, 0.8 mm, 0.9 mm, 1.0 mm).

Figure 3:
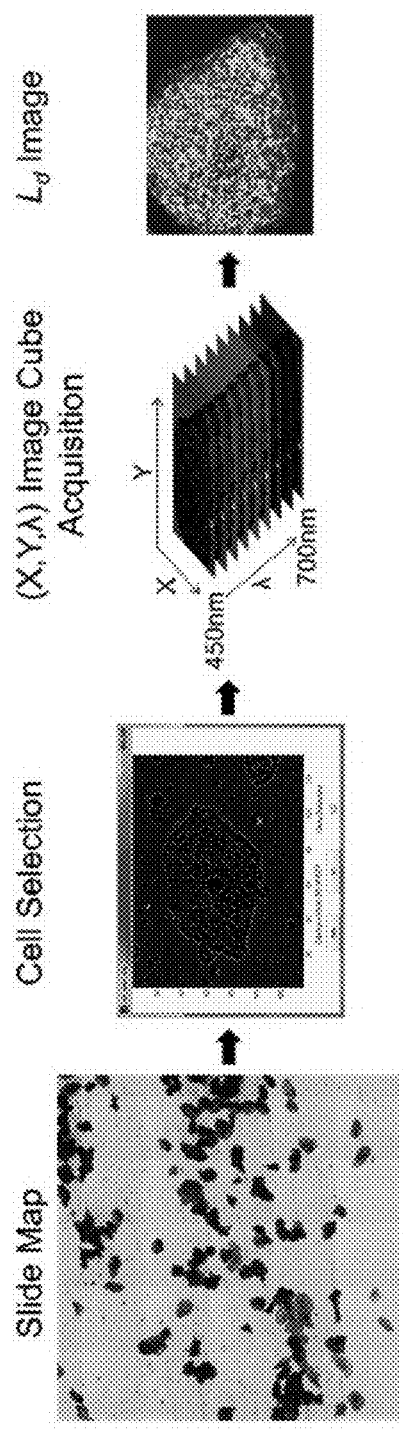
FIG. 3 illustrates a flow diagram showing an HT-PWS measurement process in accordance with aspects of the present technology.

In certain embodiments, during data acquisition scanning, the PWS instrument or system automatically moves to each selected position, autofocuses, and spectrally scans the sample collecting an image at each illumination wavelength. The result is a three dimensional data cube (x, y, $\lambda$), generated in a high throughput, automated manner. Following the collection of the data cube, the HT-PWS system can generate an image showing the nanoscale disorder strength ($L_d$) distribution within the selected target position (e.g., within a cell). FIG. 3 illustrates a flow diagram showing an HT-PWS measurement process in accordance with aspects of the present technology. In some embodiments, high-throughput/automation software and hardware increase the speed of an HT-PWS system by two orders of magnitude. For example, standard PWS data acquisition can take approximately 4-5 hours per sample (e.g., patient cell sample). High throughput/automated PWS (i.e., HT/A-PWS) can acquire data for a sample in about 1-20 minutes per sample (e.g., about 2 minutes, about 3 minutes, about 4 minutes, about 5 minutes, about 6 minutes, about 7 minutes, about 8 minutes, about 9 minutes, about 10 minutes, etc.). In addition to HT/A hardware and software, further embodiments in accordance with the present technology, include methods, processes, and/or algorithms for sample handling, data acquisition, data analysis (e.g., the algorithm for calculating intracellular nanoscale refractive index), that further increases the speed for processing a sample.

In further embodiments, a HT-PWS system or instrument can be configured to run in a variety of different data acquisition modes or sub-modes (e.g., imaging mode, diagnostic mode, etc.) in addition to the target identification and PWS data acquisition modes. In one example, if visualization of the nanoscale refractive index image of a sample is desired, the HT-PWS system can be run in an imaging mode. In another example, if the final patient diagnosis is desired, the system can be run in a diagnostic mode. In some embodiments, the type of detail, magnification, resolution, spectral bandwidth, spectral range, etc. required for a particular application is weighed against the time required for such an application in order to arrive at the optimal mode (e.g., sufficient data acquired for end use at the minimum acquisition time).

Imaging Mode:

In some embodiments, a HT-PWS system operating in imaging mode utilizes all or a portion of the HT/A hardware and software provided herein. In certain embodiments, when the system is in imaging mode, the nanoscale disorder strength $L_d$ is calculated by acquiring the entire visible spectrum (462 nm-700 nm) for each pixel within a sample (e.g., approximately 150,000 to approximately 200,000 pixels) and a disorder strength map is generated for each sample at the end of the measurement cycle. In particular embodiments, a HT-PWS system working in imaging mode acquires a desired sample measurement (e.g., a patient sample is analyzed) in approximately 5 minutes to approximately 6 minutes.

Diagnostic Mode:

In some embodiments, a HT-PWS system operating in diagnostic mode will only acquire backscattering intensity at discrete wavelengths (e.g., 2 wavelengths, 3 wavelengths, 4 wavelengths, 5 wavelength, 6 wavelengths, 7 wavelength, 8 wavelengths, etc.) instead of at the entire visible spectrum of about 462 nm to about 700 nm. In particular embodiments, a HT-PWS instrument in diagnostic mode can acquire backscattering intensity at about 500 nm, about 550 nm, about 600 nm and about 670 nm, etc. In some embodiments, average nanoscale disorder of a cell can be obtained by measuring the root-mean-square (RMS) of backscattering intensities across the pixels for each wavelength and then taking an average over different wavelengths. In some embodiments, <R>, which is used to calculate the nanoscale disorder, is calculated either by taking RMS of the backscattering spectrum or by calculating RMS of the backscattering intensity across all the pixels (V) for a given wavelength. That is, average nanoscale disorder $L_d$ of a cell 'c' is given by:

$$L_d^c \propto <(R(k)>_n \propto <(R(n)>_k.$$

Although, in some embodiments, the nanoscale disorder is calculated from a single wavelength, an average over different wavelengths that equally samples the entire visible spectrum achieves superior Signal-to-Noise (SNR) ratio. In contrast to the imaging mode wherein all the pixels in a cell are processed, the HT-PWS system running in the diagnostic mode can process only a portion of the pixels at a target location (e.g., within a cell). In particular embodiments, 10,000 or fewer pixels (e.g., 10,000 pixels, 9,000 pixels, 8,000 pixels, 7,000 pixels, 6,000 pixels, etc.), 5,000 or fewer pixels (e.g., 5,000 pixels, 4,000 pixels, 3,000 pixels, etc.), 2,500 or fewer pixels (e.g., 2,500 pixels, 2,000 pixels, 1,500 pixels, 1,000 pixels, etc.), or 1,000 or fewer pixels (e.g., 1,000 pixels, 750 pixels, 500 pixels, 200 pixels, 100 pixels, 50, etc.) are processed. Statistical calculations conducted during development of embodiments of the present technology demonstrated that processing as few as approximately 50 pixels in a cell (e.g., randomly selected, evenly distributed, etc.) increases the standard error of nanoscale disorder by about 5% and decreases the sensitivity/specificity by about 2%. In some embodiments, 5,000 pixels are used to calculate the nanoscale disorder for diagnostic mode (e.g., pre-diagnostic or screening modes may utilize fewer pixels). In contrast to the imaging mode, the nanoscale disorder image of a cell is not obtained using the HT-PWS system running in the diagnostic mode. However, the HT-PWS system working in the diagnostic mode can acquire a patient measurement (e.g., diagnostic) more rapidly (e.g., about 3 minutes or less).

In some embodiments, PWS instruments and systems as described herein can exhibit enhanced performance in addition to enhanced speed of PWS data acquisition. In some embodiments, a single high throughput PWS measurement is completed in less than 10 seconds (e.g., <5 seconds, <4 seconds, <3 seconds, <2 seconds, <1 second, etc.). In some embodiments, slide mapping is completed in less than 5 minutes (e.g., <4 minutes, <3 minutes, <2 minutes, <1 minute, etc.) depending on the size of the region required and the size of the target (e.g., cells) being measured. In certain embodiments, automated cell selection using the image segmentation and cell identification algorithm is performed while the slide map is generated. In one particular example, PWS data acquisition is completed in less than 5 seconds, slide mapping can be completed in about 2 minutes, and automated cell selection can be performed while the slide map is generated. Thus, in some embodiments, acquisition of PWS data for a single patient specimen (e.g., approximately 30 cells) can be completed in about 3 minutes via HT-PWS. Furthermore, HT-PWS does not sacrifice image quality, resolution, magnification, and/or completeness.

In some embodiments, operation of all or a portion of the functions of a HT-PWS instrument are controlled via user interfaces (e.g., graphical user interfaces (GUI), computer workstations, etc.). A user interface may be integral to the instrument, part of a connected system with the instrument, and/or a stand-alone unit (e.g., a separate computer that interacts with the instrument). In some embodiments, a user interface accepts parameters or other input from a user. In particular embodiments, a PWS instrument automatically performs all or a portion the functions of a PWS instrument (e.g., based on user input parameters). In some embodiments, a user interface allows a user to provide parameters and/or instructions to a processor that directs the functions of a PWS instrument. In some embodiments, a user enters custom parameters and/or instructions, selects from a library of preset parameters and instructions, or a combination thereof. In various embodiments, once a user has entered parameters (e.g., number of samples, number of targets per sample, resolution of data acquisitions, the number of wavelengths, instrument acquisition time, etc.) and initiated a run procedure, the PWS instrument (via, for example, software, processor, controller, etc.) performs all scanning, sample handling, and data acquisition steps without additional user input or intervention. In some embodiments, all or a portion of data analysis is automatically performed by the PWS instrument. In some embodiments, one or more of acquired data, raw data, analyzed data, results, analysis, diagnosis, conclusions, scan performance, etc., are provided to a user of the system via a user interface. In some embodiments, a report is generated as a result of a PWS session (e.g., one report per sample, one report per run, etc.) which is displayed on the user interface, printed, or otherwise communicated (e.g., via a server, via email, via mail, etc.) to the operator, a clinician, a patient, a researcher, etc. In some embodiments, any or all of the steps of target identification, data acquisition, sample manipulation, data analysis, and reporting of results are automated by the software, hardware, and processor(s) integral to or in communication with a PWS instrument.

C. Additional Examples

Example 1

Nanostructured Phantoms

Figure 4:
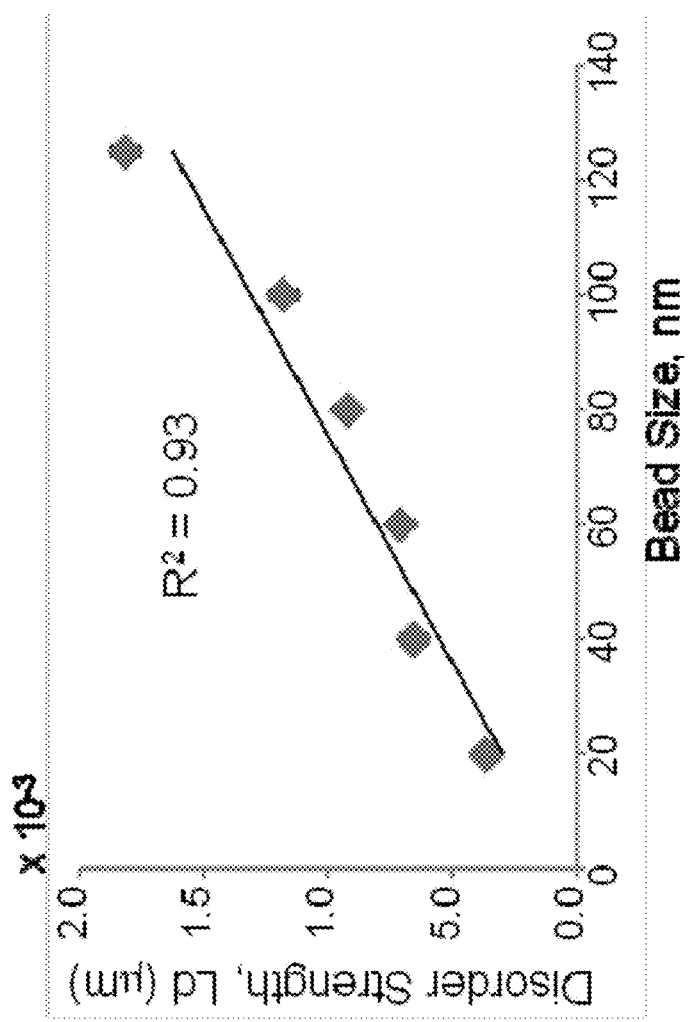
FIG. 4 graphically illustrates HT-PWS detection of variable sized nanoscale structures in accordance with an embodiment of the technology.

The nanoscale sensitivity of a High Throughput PWS Microscope was verified by performing experiments on a series of known nanostructured models comprised of aggregated polystyrene nanospheres. The nanosphere phantoms were prepared as follows: the aqueous suspension of monodispersed nanospheres (available from Thermo Fisher Scientific, Inc. of 81 Wyman St., Waltham, Mass. 02451) was uniformly smeared on a flat surface of a slide to form a self-assembled lattice. The models were constructed with thickness varying from 2.5 µm to 3 µm (e.g., to mimic cell thickness) using nanospheres of sizes 20 nm to 125 nm. PWS measurements were taken from phantoms of different thickness and nanosphere sizes. The advantage of this nanostructure model is that both Lc and Δn are known a priori (e.g., Lc corresponds to the size of a nanosphere, Δn corresponds to the refractive index of a nanosphere). Twenty-five measurements were acquired from each phantom at different positions to allow for statistical comparison of the data. In order to compare phantoms comprised of spheres of different diameters, measurements were acquired in each phantom from regions of similar thickness based on the number of spectral oscillations (5 to 7 oscillations or 2.5 to 3.5 µm). For each phantom, 25 regions of interest were selected, and $L_d$ analysis was performed on the pixels in these regions. As shown in FIG. 4, the $L_d$ measurements were plotted as a function of the phantom nanosphere size to demonstrate sensitivity of $L_d$ to nanoscale length scales. In analysis of this example, the lengthscale dependence of $L_d$ can be observed as $L_d$ values show a steadily increasing trend with increasing diameter of the nanospheres making up the phantoms. Correlation between the lengthscale of phantom spheres and $L_d$ is linear with an $R^2$ value of 0.93.

Example 2

Human Colon Carcinoma Cell Lines

This section describes an example of the diagnostic capability of the HT-PWS system in accordance with aspects of the present technology, and as established on human colon cancer cell lines (HT29 cells) and genetic knockdown variants (EGFR knockdown cells). The experiment consisted of two groups, control vector HT29 (CV) cells and epidermal growth factor receptor (EGFR) knockdown HT29 cells, a less aggressive genetic variant. In particular, an Sh-RNA approach was used against a proto-oncogene, epidermal growth factor receptor (EGFR) in the human colon cancer cell line HT-29. The knockdown was modest (<50%) and hence the cell lines were microscopically indistinguishable.

The HT29 control vector and EGFR knockdown cells were first collected in centrifuge tubes and centrifuged for 5 min at 1000 rpm. The supernatant was then removed, and the cells were plated on a glass chamber slide. The slides were checked to ensure that they contained at least 20,000 cells. Two milliliters of fresh cell culture medium was added to each chamber slide, which was then incubated at 37° C. for at least 5 to 6 h. After incubation, the medium was completely removed from the chamber slides, and the slides were washed with 70% ethanol to remove any traces of the medium. Following this, the slides were immediately fixed using 70% ethanol and kept in a 4° C. refrigerator until PWS measurements. Using this protocol, one slide each was prepared of control vector HT29 cells and one of EGFR knockdown HT29 cells. The two slides were measured unstained on both a conventional spectrometer-based PWS system (e.g., non-HT, non-automated) and the HT-PWS system as disclosed herein. The same 25 cells from each cell line were measured to allow for statistical comparison of the data.

Figure 5A:
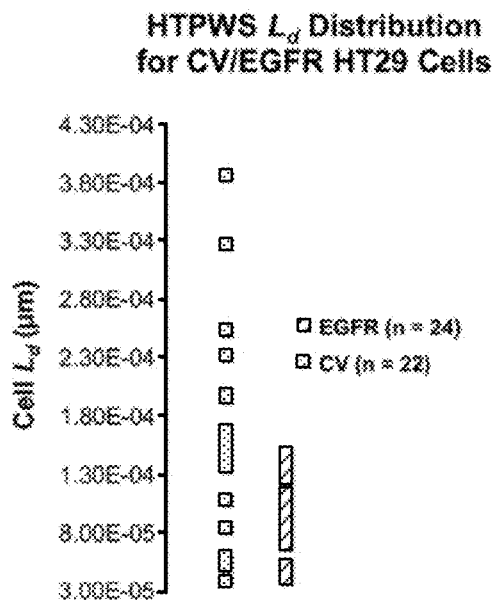
FIGS. 5A-5B are display diagrams illustrating data results from one particular study to illustrate diagnostic screening of cancer cells using HT-PWS.
Figure 5B:
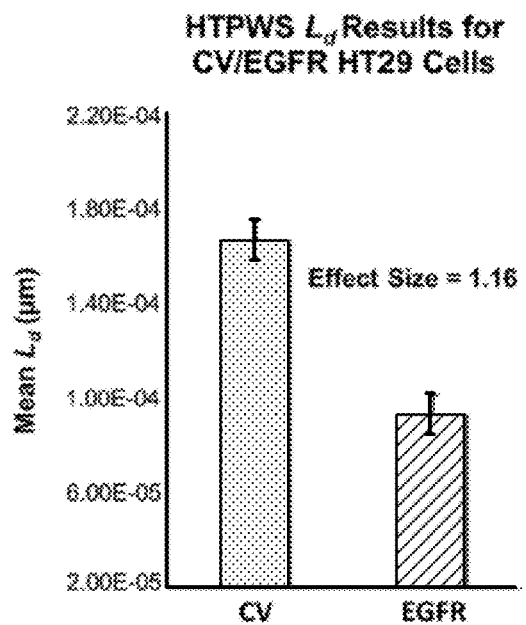

FIGS. 5A and 5B show distribution, average $L_d$ values, and the corresponding effect size for the CV and the EGFR knockdown cells using the HT-PWS system. Comparison of the results from both the conventional PWS system and the HT-PWS system shows similar effect sizes for the differences between the mean $L_d$ values for the CV and EGFR cell types: 1.16 for the HT-PWS system (FIG. 5B) and 1.23 for the conventional spectrometer-based PWS system, respectively. P values were also comparable with 0.0007 for the HT-PWS system and 0.0002 for the conventional spectrometer-based PWS system.

Example 3

Human Lung Cancer

Figure 6A:
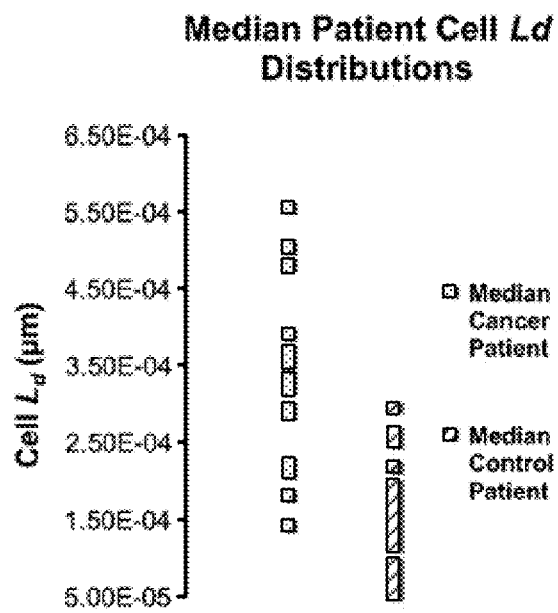
FIGS. 6A-6B are display diagrams illustrating data results from another study to determine lung cancer diagnostic performance with an HT-PWS system in accordance with various embodiments of the present technology.
Figure 6B:
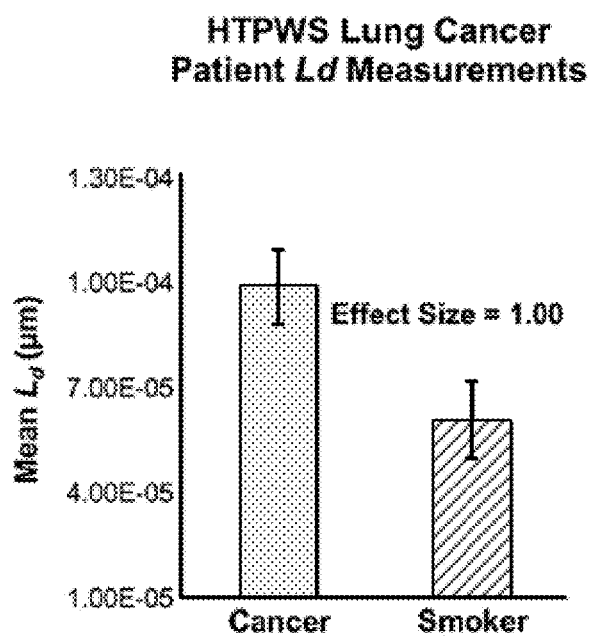

This section describes an example of clinical lung cancer diagnostic performance with an HT-PWS system in accordance with various embodiments of the present technology. Evaluation of 23 human patients, consisting of 9 patients with cancer and 14 smokers, was performed in accordance with the Institutional Review Board at NorthShore University HealthSystem. Cells were brushed from each patient's cheek and smeared onto a glass slide before being fixed in 95% ethanol and stained using Papanicolaou stain just prior to PWS measurement. For each patient, approximately 30 cells were measured and used to determine mean $L_d$ values for the individual patients as well as for each diagnostic category (FIGS. 6A-6B). Measurements were also performed on a conventional PWS system to correlate $L_d$ measurements between the conventional PWS system and the HT-PWS system as disclosed herein. Diagnostic performance of the HT-PWS system was represented by quantifying the difference in the mean $L_d$'s of the cancer and smoker patient groups using the data collected from all 23 patients (FIG. 6B). Average $L_d$ measurements were computed for each patient and for two groups, patients with cancer and patients who are smokers. As shown in FIG. 6B, the cancer group had a significantly higher average $L_d$ compared with the smoker group as measured with the HT-PWS instrument, p=0.02 and effect size=1.00.

Figure 7:
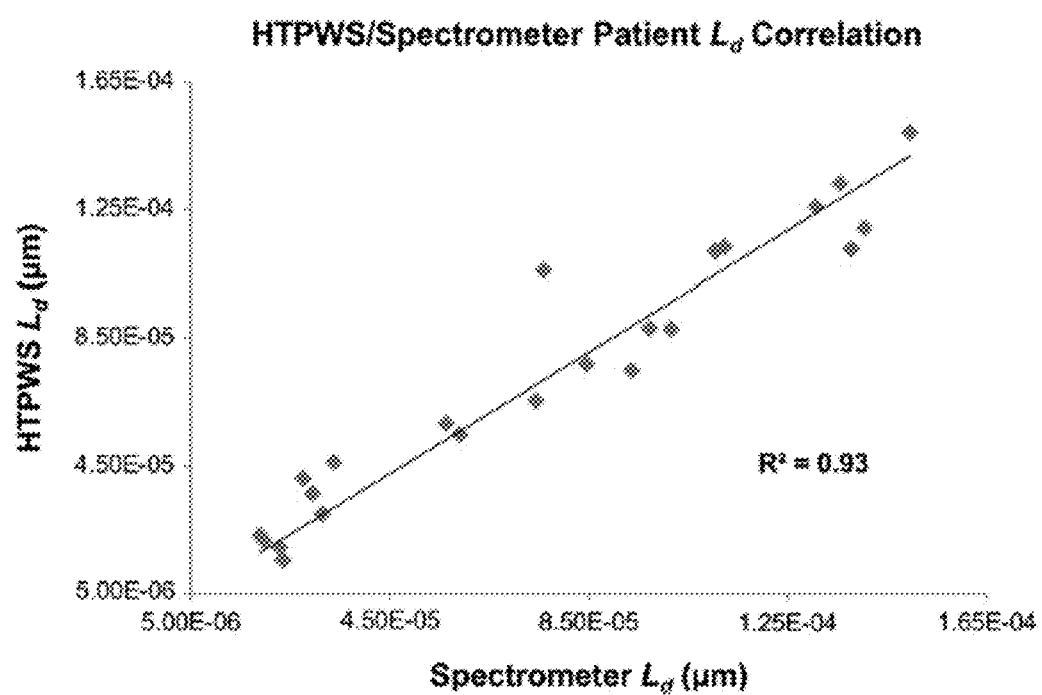
FIG. 7 graphically illustrates the correlation between patient $L_d$ values generated by the conventional PWS system and the HT-PWS system in the diagnosis of lung cancer cells in accordance with various embodiments of the present technology.

Similar results to those in FIGS. 6A-6B were achieved with the conventional PWS system. Cancer patients had significantly higher $L_d$ values than smokers with p=0.03 and effect size=0.90. To verify consistent results between the conventional PWS system and the HT-PWS system, correlation between individual cell $L_d$ values and patient $L_d$ values was plotted for the two systems. FIG. 7 shows the correlation between patient $L_d$ values for the conventional PWS system and the HT-PWS system. The correlation between the patient $L_d$ values for the conventional PWS system and the HT-PWS system yielded $R^2$=0.93. For individual cell $L_d$ values, the correlation was $R^2$=0.92.

CONCLUSION

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, one or more modules or components of the HT-PWS system (e.g., AOTF, controller/processor, software and/or algorithmic instructions for automated operation of the HT-PWS system and processing of the PWS data) can be configured to be incorporated with or operate with conventional PWS microscopes to provide a high throughput PWS system as described herein. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A method of selecting one or more target locations on a sample-containing substrate for partial wave spectroscopy (PWS) microscopy, comprising:
    (a) creating an image of the substrate at a first magnification using a PWS system; and
    (b) selecting the one or more target locations on the substrate for PWS microscopy at a second magnification based on the image, wherein the second magnification is higher than the first magnification.

2. The method of claim 1, wherein the one or more target locations comprise one or more cells with target-cell characteristics.

3. The method of claim 2, wherein the target-cell characteristics are selected from the group consisting of size, morphology, positioning on the slide, and spacing between cells.

4. The method of claim 2, wherein the target-cell characteristics are selected automatically by a selection algorithm.

5. The method of claim 1, wherein the step of creating an image of the substrate at a first magnification, comprises:
    (i) collecting multiple images of the substrate at the first magnification; and
    (ii) tiling the multiple images together to create a single larger image of the substrate.

6. The method of claim 5, further comprising:
    measured autofocusing the PWS system prior to collecting a first image of the multiple images of the substrate at the first magnification; and
    periodically repeating measured autofocusing of the PWS system during the collection of the multiple images.

7. The method of claim 6, wherein a predictive autofocusing algorithm is used to focus the PWS system between instances of measured autofocusing.

8. A method of analyzing a sample by high-throughput partial wave spectroscopy (PWS) microscopy, comprising:
(a) selecting target locations on a sample-containing substrate, wherein selecting includes—
creating an image of the substrate at a first magnification using PWS microscopy; and
selecting one or more target locations on the substrate for PWS microscopy at a second magnification based on the image, wherein the second magnification is higher than the first magnification; and
(b) obtaining PWS measurements of the one or more target locations at the second magnification.

9. The method of claim 8, wherein obtaining PWS measurements comprises automatically:
(i) centering a high throughput PWS system on a first target location;
(ii) autofocusing the system on the first target location;
(iii) spectrally scanning the first target location at a range of illumination wavelengths; and
(iv) collecting a PWS image at each illumination wavelength.

10. The method of claim 9, wherein steps (iii) and (iv) comprise illuminating a target location with a wavelength of light and collecting a PWS image for each stepwise wavelength in said range of illumination wavelengths.

11. The method of claim 9, wherein said range of illumination wavelengths comprises about 462 nm-700 nm.

12. The method of claim 8, further comprising collecting a partial wave spectroscopy x/y/λ-data cube of the target location, wherein collecting includes:
focusing a partial wave spectroscopy (PWS) system on an x/y target location; and
spectrally scanning the x/y target location while collecting an x/y image at each illumination wavelength of the spectral scan.

13. The method of claim 12, wherein spectrally scanning comprises illuminating the x/y target location at a series of illumination wavelengths throughout a spectrum and collecting an image at each wavelength.

14. The method of claim 13, where each illumination wavelength in the series of illumination wavelengths are about 1 nm to about 10 nm apart.

15. The method of claim 12, wherein the x/y image is the result of collected backscattered light from the x/y target location.

16. A partial wave spectroscopy (PWS) system, comprising:
a tunable illumination system to provide a broad spectrum of incident light on a target; and
a receiving end positioned in an imaging plane of the system to separately record intensity of multiple spectra of backscattered light from one or more preselected areas of the target illuminated with the incident light, wherein the multiple spectra of emergent light results from refractive index fluctuations within the target.

17. The PWS system of claim 16, wherein the incident light is from a light source focused through an acousto-optic tunable filter.

18. The PWS system of claim 17, wherein the incident light exiting from said acousto-optic tunable filter is focused through an aperture configured to provide an illumination numerical aperture (NA).

19. The PWS system of claim 16, wherein the receiving end comprises an imaging spectrograph configured to receive at least two distinct spectra within a broad spectrum of incident light.

20. The PWS system of claim 16, wherein the receiving end records spectral information on a cell-by-cell basis.

21. The PWS system of claim 18, wherein the aperture is an electronic and/or motorized aperture.

22. The PWS system of claim 18, wherein the incident light exiting the aperture is collimated, passed through a field aperture, and focused onto a back focal plane of an objective lens.

23. The PWS system of claim 16, wherein the PWS system further comprises components for automated high throughput PWS selected from the group consisting of: an automated stage, an automated objective turret, a second aperture to control an angle of collected backscattered light, and hardware triggers between the acousto-optic tunable filter and the receiving end to synchronization wavelength tuning and image capture.

24. The PWS system of claim 18, wherein the aperture is configured to set a low illumination NA to reduce an angle of emitted incident light.

25. The PWS system of claim 23, wherein the second aperture is an electronic and/or motorized second aperture.

26. The PWS system of claim 23, wherein the second aperture is configured to set a high collection NA to sharpen the PWS image.

* * * * *